United States Patent
Chabiniok et al.

(10) Patent No.: US 11,957,437 B2
(45) Date of Patent: Apr. 16, 2024

(54) CARDIAC DEVICE

(71) Applicants: INRIA INSTITUT NATIONAL DE RECHERCHE EN INFORMATIQUE ET EN AUTOMATIQUE, Le Chesnay (FR); ASSISTANCE PUBLIQUE HOPITAUX DE PARIS, Paris (FR)

(72) Inventors: Radomir Chabiniok, Paris (FR); Dominique Chapelle, Paris (FR); Arthur Le Gall, Paris (FR); Philippe Moireau, Gif sur Yvette (FR); Fabrice Vallee, Les Lilas (FR)

(73) Assignees: Inria Institut National De Recherche En Informatique Et En Automatique, Le Chesnay (FR); Assitance Publique Hopitaux, Paris (FR)

( * ) Notice: Subject to any disclaimer, the term of this patent is extended or adjusted under 35 U.S.C. 154(b) by 401 days.

(21) Appl. No.: 16/643,078

(22) PCT Filed: Aug. 28, 2018

(86) PCT No.: PCT/FR2018/052111
§ 371 (c)(1),
(2) Date: Feb. 28, 2020

(87) PCT Pub. No.: WO2019/043328
PCT Pub. Date: Mar. 7, 2019

(65) Prior Publication Data
US 2020/0253490 A1    Aug. 13, 2020

(30) Foreign Application Priority Data
Aug. 30, 2017   (FR) .......................... 1758006

(51) Int. Cl.
A61B 5/02       (2006.01)
A61B 5/00       (2006.01)
(Continued)

(52) U.S. Cl.
CPC .......... *A61B 5/02028* (2013.01); *A61B 5/021* (2013.01); *A61B 5/4821* (2013.01);
(Continued)

(58) Field of Classification Search
CPC ... A61B 5/02028; A61B 5/021; A61B 5/4821; A61B 5/4848; A61B 5/725; G16H 50/50
See application file for complete search history.

(56) References Cited

U.S. PATENT DOCUMENTS

2014/0275886 A1    9/2014  Teixeira et al.
2016/0196384 A1 *  7/2016  Mansi ................. G16H 30/20
                                               600/408
(Continued)

FOREIGN PATENT DOCUMENTS

AU    2014250646 A1 *  11/2014  ......... A61B 5/02028
CN    1698534 A         11/2005
(Continued)

OTHER PUBLICATIONS

Chin-en Kuo, et al., "Estimation and Prediction of Propafenone on the Termination of Atrial Fibrillation by State-Space Models," Computer Symposium (ICS), 2010 IEEE International, Piscataway, NJ, 2010, pp. 841-845.
(Continued)

*Primary Examiner* — Carl H Layno
*Assistant Examiner* — Aya Ziad Bakkar
(74) *Attorney, Agent, or Firm* — Maynard Nexsen PC; Brian T. Sattizahn

(57) ABSTRACT

A cardiac device comprises a memory arranged for receiving haemodynamic data, and a computer arranged for applying a cardiovascular model comprising a cardiac model and an arterial and venous blood circulation model using the data received in the memory, and for extracting therefrom at least one cardiac activity indicator (CI).

4 Claims, 4 Drawing Sheets

(51) Int. Cl.
*A61B 5/021* (2006.01)
*G16H 50/50* (2018.01)

(52) U.S. Cl.
CPC .......... *A61B 5/4848* (2013.01); *A61B 5/725* (2013.01); *G16H 50/50* (2018.01)

(56) References Cited

U.S. PATENT DOCUMENTS

2017/0000389 A1* 1/2017 Davidson .............. A61B 5/1112
2017/0235915 A1* 8/2017 Mansi ................... G16H 50/30
                                                                                  705/3

FOREIGN PATENT DOCUMENTS

| CN | 1925785 A | 3/2007 |
| CN | 105852841 A | 8/2016 |
| CN | 105976348 A | 9/2016 |
| EP | 1598005 A1 | 11/2005 |
| EP | 3043276 A2 | 7/2016 |
| FR | 3048352 A1 | 9/2017 |
| JP | 2005253657 A | 9/2005 |
| JP | 2005312947 A | 11/2005 |
| JP | 2008536567 A | 9/2008 |
| WO | 2014162181 A2 | 10/2014 |

OTHER PUBLICATIONS

Caruel, et al., "Dimensional reductions of a cardiac model for effective validation and calibration," Biomechanics and Modeling in Mechanobiology, Springer Verlag, 2014, 13 (4), pp. 897-914.

Chapelle, et al., "Patient-Specific Biomechanical Modeling of Cardiac Amyloidosis—A Case Study," Functional Imaging and Modeling of the Heart 2015, Jun. 2015, Maastricht, Netherlands, pp. 295-303.

Moireau, et al., "Joint state and parameter estimation for distributed mechanical systems," Computer Methods in Applied Mechanics and Engineering, Elsevier, 2008, 197 (6-8), pp. 659-677.

Laurin, et al., "A 3D Model of the Thorax for Seismocardiography," Computing in Cardiology, 2015, pp. 465-468, vol. 42.

First Office Action mailed on Aug. 10, 2022 in Chinese Patent Application No. 201880056096, filed on Aug. 28, 2018, 10 Pages (Including English-Language Translation).

First Search mailed on Sep. 26, 2022 in Chinese Patent Application No. 201880056096, filed on Aug. 28, 2018, 2 Pages.

International Search Report and Written Opinion mailed on Mar. 7, 2019 in International Patent Application No. PCT/FR2018/052111, filed on Aug. 28, 2018, 10 Pages.

Notice of Reasons for Refusal, mailed on Jul. 26, 2022 in Japanese Patent Application No. 2020512585, filed on Aug. 28, 2018, 6 Pages (Including English-Language Translation).

* cited by examiner

CARDIAC DEVICE

The invention relates to the field of anaesthesia and intensive care cardiac monitoring.

BACKGROUND OF THE INVENTION

Haemodynamic instability in the operating theatre is frequent and the causes thereof are varied (surgery, heart failure, vasodilation, etc.). Physiopathological understanding is required to be able to anticipate, identify, and treat these events and/or the consequences thereof. Thus, it is recommended to monitor cardiovascular status and function indicators, such as continuous blood pressure and cardiac output by transoesophageal Doppler, of patients at risk of intraoperative events. However, in the most complex cases, analyses of blood pressure and aortic blood velocity measurements, only partially accounting for interactions between the heart and the vessels, may be insufficient to manage the cardiovascular intensive care strategy in the operating theatre.

Digital modelling makes it possible moreover to simulate the behaviour of the cardiovascular system, and extract from the simulation indicators normally inaccessible by non-invasive and/or continuous monitoring, such as the ventricular pressure/volume curve. However, the quality and precision of the indicators from these simulations can only be obtained by jointly processing sufficiently rich data to make it possible to adapt the parameters of the model, by so-called data assimilation methods, so as to approximate the cardiovascular status of the patient in question.

SUMMARY OF THE INVENTION

The invention improves the situation. To this end, the invention relates to a cardiac device for real-time cardiovascular monitoring carried out in anaesthesia and intensive care which comprises a memory arranged for receiving haemodynamic data, and a computer arranged for applying a cardiovascular model comprising a cardiac model and an arterial and venous blood circulation model based on the data received in the memory, and for deriving therefrom at least one cardiac activity indicator.

This device makes it possible to improve the cardiovascular monitoring carried out in anaesthesia and intensive care, using real-time simulations of a digital cardiovascular model, with joint processing of the haemodynamic monitoring data to adapt the model continuously, and thus extract therefrom indicators inaccessible in the data alone (for example ventricular pressure/volume curves, vascular resistance or myocardial strain). Optionally, the model may include pharmacological inputs suitable for predicting the effects of the medicinal products used in anaesthesia and intensive care. Thus, the simulation will also enable the use of proactive loops for administering medicinal products, leading to the automation of the administration thereof.

In various alternative embodiments, the invention may have one or a plurality of the following features:
the computer is arranged for computing a cardiac activity indicator, by applying a cardiovascular model to compute an arterial pressure value and a cardiac output value that are theoretical, and by applying at least one correction function based on the difference between the arterial pressure value and a cardiac output value that are theoretical and haemodynamic data received in the memory,
the computer is arranged for applying at least one Kalman filter or a combination of a Kalman filter with a Luenberger observer in said at least one correction function, and
the computer is further arranged for applying the arterial and venous blood circulation model with a pharmacological model.

The invention also relates to a cardiac monitoring method comprising:
receiving haemodynamic data,
applying a cardiovascular model comprising a cardiac model and an arterial and venous blood circulation model to the haemodynamic data, and deriving therefrom at least one cardiac activity indicator.

BRIEF DESCRIPTION OF THE DRAWINGS

Further features and advantages of the invention will emerge more clearly on reading the following description, based on examples given by way of illustration and not limitation, based on drawings wherein.

The drawings and the description hereinafter contain, essentially, elements of certain nature. They may therefore not only serve to better convey the present invention, but also contribute to the definition thereof, if applicable.

DETAILED DESCRIPTION

The present description may include elements subject to royalty and/or copyright protection. The rights holder has no objection to the identical reproduction by any party of the present patent document or of the description thereof, as it appears in official records. For the rest, it reserves its rights completely.

Furthermore, the detailed description is extended with appendix A, which gives the formulation of certain mathematical formulas used according to the invention. This Appendix is set apart for clarification purposes, and to facilitate references. It is an integral part of the description, and may therefore not only serve to better convey the present invention, but also contribute to the definition therefore, if applicable.

Figure 1:
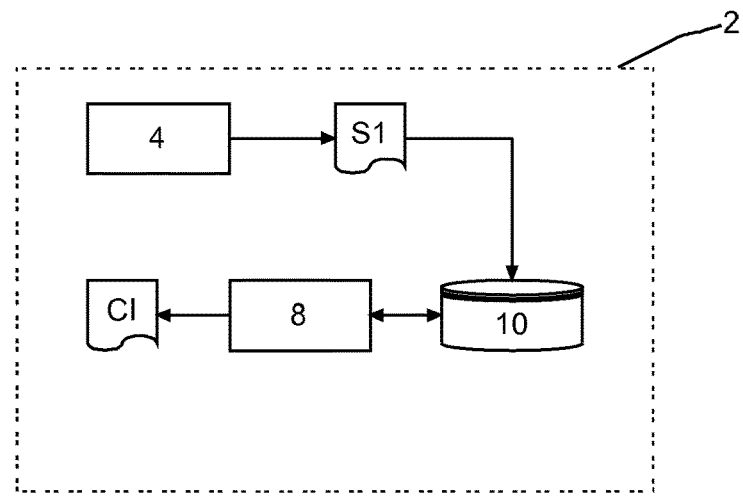
FIG. 1 represents a general diagram of a device according to the invention.

FIG. 1 represents a general diagram of a device 2 according to the invention. The device 2 comprises a haemodynamic measurement acquisition system 4, a computer 8 and a memory 10.

In the example described herein, the device 2 is a device suitable for being used in an operating theatre. More particularly, it may be incorporated in an existing anaesthetic monitoring device, so as to save space. Alternatively, the device 2 could be produced separately, and receive the anaesthetic monitoring data required for the operation thereof. Also alternatively, the elements of the device 2 could be produced separately.

According to the invention, the computer 8 is an element accessing the memory 10 directly or indirectly. It may be embodied in the form of a suitable computer code executed on one or a plurality of processors. Processors should be understood as referring to any suitable processor. Such a processor may be embodied in any known manner, in the form of a personal computer microprocessor, a dedicated chip of the FPGA or SoC ("system on chip") type, a grid computing resource, a microcontroller, or any other form suitable for supplying the computing power required for the embodiment described hereinafter. One or a plurality of these elements may also be embodied in the form of specialised electronic circuits such as an ASIC. A combination of processor and electronic circuits may also be envisaged.

According to the invention, the memory 10 may be any type of data storage suitable for receiving digital data: hard drive, flash memory hard drive (SSD), flash memory in any form, random-access memory, magnetic disk, locally distributed or cloud storage, etc. The data computed by the device may be stored on any type of memory similar to the memory 10, or thereon. These data may be deleted after the device has performed the tasks thereof, or stored.

In the example described herein, the haemodynamic measurement acquisition system 4 is a Philips Intellivue MP60 type monitor suitable for connecting various electronic sources, themselves measuring haemodynamic indicators (such as the arterial pressure, or the cardiac output). The haemodynamic measurement acquisition system 4 measures the arterial pressure and the aortic output in real time.

The cardiovascular model comprises:
a cardiac model linking heart modelling parameters (modulus of elasticity, contractility, maximum active tension of muscle fibres, etc.) and variables representative of the status of the heart, particularly describing the deformations thereof, and
an arterial and venous blood circulation model also linking parameters (arterial elastances, peripheral resistances, etc.), and state variables (particularly arterial and venous pressures).

In the case described herein, the cardiac quantities that a clinician will seek to monitor comprise the left ventricular volume variation (linked with the cavity radius variation, hereinafter annotated y), the muscle fibre deformation (hereinafter ec), the active cardiac stiffness (hereinafter kc), the active cardiac stress (hereinafter tc), the aortic pressure (hereinafter Par), and the distal arterial pressure (hereinafter Pd). These characteristic quantities of cardiac function status will be hereinafter compiled in a vector xc. Further quantities of interest relate to certain modelling parameters suitable for progressing over time according to the patient's status, and these parameters comprise particularly the contractility (hereinafter s0), the active stiffness (hereinafter k0), and the peripheral resistance (hereinafter Rd). These parameters are compiled in an vector annotated T. Finally, varied indicators may be derived from the vector xc and from the modelling parameters T to make it possible to monitor the progression of the cardiovascular system. These indicators, particularly comprising the cardiac output (hereinafter Qc), will be hereinafter designated by a vector CI.

The vector xc and the vector T are linked by equations (10) to (70) of Appendix A, wherein equations (10), (20), (30), (40), (50), (60) and (70) denote the independent relations, and equations (11) to (18) define the sides of equation (10). The quantity $\bar{u}$ denotes a fixed-time function (activation function), and n0 a function of the deformation ec modulating the active tension (Starling effect). The article by M. Caruel et al, "*Dimensional reductions of a cardiac model for effective validation and calibration*", Biomech Model Mechanobiol, 2013 describes these equations in detail.

The system formed by equations (10) to (70) can be summarised in the form of equation (80).

Once this cardiac model has been established, an arterio-venous coupling model may be used. This model makes it possible to establish an atrial pressure value Pat (also referred to as preload). Indeed, the atrial pressure cannot be known via continuous measurements, and is an extremely useful indicator of a patient's cardiac status.

The arterio-venous coupling is expressed by establishing, on one hand, the equilibrium between the output of the arterial compartment and the venous compartment, and using the definition of the output of the venous compartment as a smoothing of the cardiac output.

This gives equation (90), wherein the left side represents the blood flow passing through the capillaries, dependent on the difference in pressure between the arterial compartment and the venous compartment and using a blood volume conservation relation, and the right side represents the definition of the output of the venous compartment (Qsv) as a smoothing of the cardiac output (Qc), as viewed via the capillaries.

In the left side, the value Veff represents the effective blood volume involved in arterio-venous exchanges, whereas the value Csv represents the compliance of the venous system, or storage capacity at the venous end. In the right side, the exponential formula serves to model a memory effect in order to smooth the output in the veins when the heart is not expelling blood, and the expression in the denominator represents a normalising constant. The article by D. Chapelle et al, "*Patient-specific biomechanical modeling of cardiac amyloidosis—A case study*", Proc. of FIMH 2015, LNCS Vol. 9126, pp. 295-303, Springer 2015 describes these equations in detail.

Equation (90) can therefore be used to determine the pressure in the venous system (Psv), and derive the atrial pressure (Pat) therefrom according to equation (100) of Appendix A. In this equation, a function is added to the venous system pressure in order to account for the increase in pressure induced by the contraction of the atrium at the start of the cardiac cycle. This function is typically an upward gradient, followed by a plateau and a downward gradient, which is repeated with each cardiac cycle.

In an ideal scenario, it would therefore be possible to use these equations for determining everything instantaneously. For this, it is necessary to start from the measurements, defined by the theoretical measurement z(t) in equation (110) of Appendix A. However, while the model simulations can be compared to the measurements, this sequence of operations is not invertible, it is thus not possible to directly determine the status and parameters of the model to match it to the patient's current status.

In order to remedy this problem, associated with the fact that the operator Ac is not necessarily invertible, the Applicant has devised a function Calc( ) which supplements the model described above, and has discretised the latter.

To continuously adjust the model to the patient, the Applicant has introduced with equation (120) an innovation vector which measures the difference between the denoised measurement Z(t) and the theoretical measurement z(t). The innovation vector is then reintroduced into correction functions based on a Kalman filter, or on a combination of a Kalman filter with a Luenberger observer as disclosed in the article by Moireau et al. "*Joint state and parameter estimation for distributed mechanical systems*", Comput. Methods Appl. Mech. Engrg. 197 (2008) 659-677. These correction functions have the advantage of ensuring convergence in a wide range of scenarios, in a few operating loops.

Accordingly, the Applicant has introduced equation (180) to modify equation (80) so as to account for these corrections, and introduced equation (185) to account for the effects thereof on the vector T.

The computer 8 may also receive signals measured by other sensors, particularly localised non-invasive pressure measurements for example on the finger or at the common carotid, data obtained from the respirator (airway pressure, insufflation flow rate, current volume, etc.), electroencephalographic and electrocardiographic data, near-infrared spectroscopy cerebral oximetry, pulsed oxygen saturation or cutaneous oxygen or $CO_2$ pressure measurements, or invasive pressure and flow measurements obtained by direct catheterisation, but also the intracranial pressure. These additional measurements are then combined with the cardiac data determined by the computer 8 to derive therefrom cardiac indicators for monitoring specific cardiac diseases.

Figure 2:
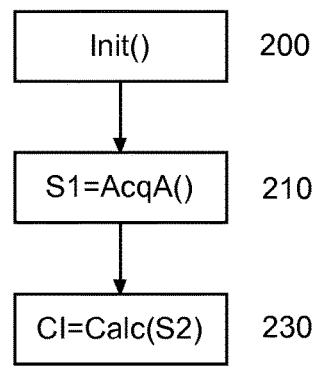
FIG. 2 represents an example of embodiment of a function executed by the device in FIG. 1.

FIG. 2 represents an example of a function used by the device 2. In an operation 200, the device 2 executes a function Init( ). The function Init( ) initialises the device 2, particularly by selecting patient-specific parameters relative to the cardiovascular model. This function may carry out a calibration operation each time the device 2 is started, or carry out this calibration periodically or once and for all.

Then, in an operation of 210, haemodynamic signal acquisition is carried out. In the example described herein, this involves arterial haemodynamic variables, namely the arterial pressure and the aortic flow.

Finally, in an operation of 230, the computer 8 executes a function Calc( ) which applies the cardiovascular model to the signals to derive the cardiac data CI therefrom.

Figure 3:
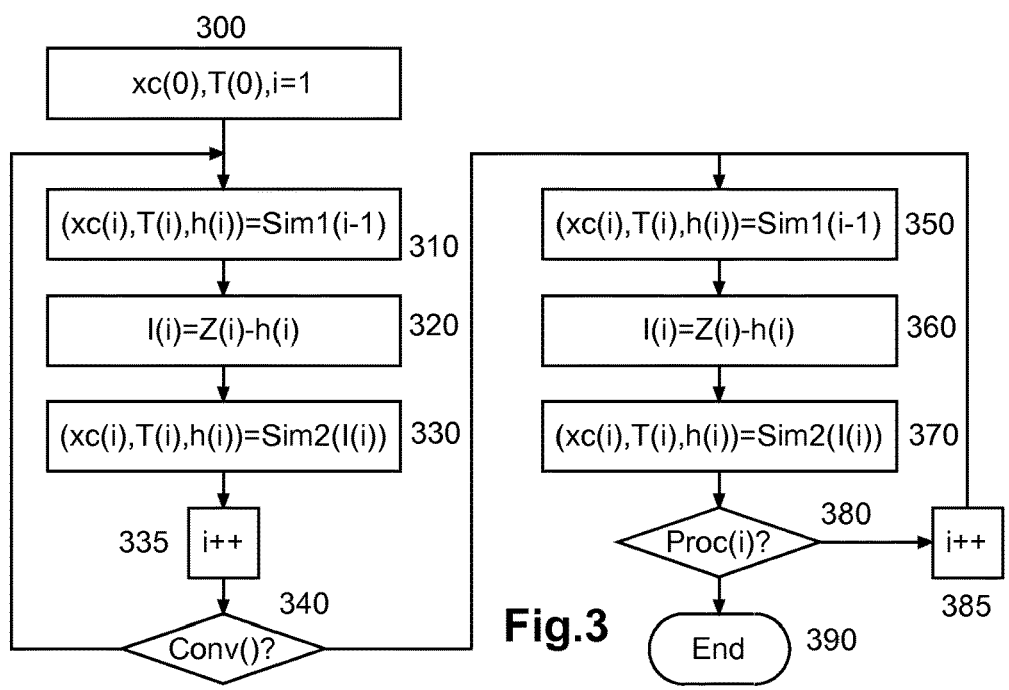
FIG. 3 represents an example of embodiment of an operation in FIG. 2, and FIGS. 4 to 8 represent examples of clinical signals obtained and processed by the device in FIG. 1.

FIG. 3 represents an example of embodiment of the function Calc( ).

The function Calc( ) comprises two loops with identical functioning, the first whereof serves for initialisation and the second for processing.

In an operation 300, the function Calc( ) starts with initialisation values of the vectors xc and T, as well as with a time index i.

Then, in an operation 310, a function Sim1( ) is applied with by way of argument the index i-1. The function Sim1( ) applies sequentially a discretised version of equations (80) to (110), so as to determine what the value of z(t) would be for the time corresponding to the time i, as computed according to the theoretical model. This value is designated by h(i).

Equations (280) and (310) represent a possible discretised version, by a so-called explicit method, of equations (80) and (110) applied by the function Sim1( ). Then, in an operation 320, the computer 8 computes the innovation vector by applying equation (120), and the simulation is repeated in an operation 330 with a function Sim2( ).

The function Sim2( ) receives the innovation vector I(i) to apply equations (180) and (185), in a discretised form in the same manner as equations (280) and (310), as this appears with equations (380) to (410). In practice, the function Sim2( ) applies a correction derived from the innovation vector to the computations previously carried out with the function Sim1( ). Alternatively, the function Sim2( ) could resume the computations entirely.

Then, in an operation 335, the index i is incremented, and, a function Conv( ) is executed in an operation 340 to compare the difference between the value h(i) obtained from the operation 330 and the measurement Z(i) obtained from the haemodynamic signals used in the operation 320.

When this difference is greater than a chosen threshold, then it is considered that the correction functions are not yet sufficient, and the function Calc( ) resumes with the operation 310.

As mentioned previously, the convergence by the correction functions is attained relatively quickly, for example from the haemodynamic measurements associated with a single heartbeat.

When the difference is less than the chosen threshold, then it is considered that the values determined are useful, and the second loop starts.

In the second loop, operations 350 to 370 identical to the operations 310 to 330 are executed in order to determine the current values of the vector xt(i) and T(i). Then, in an operation 380, these measurements are displayed and/or undergo processing relating to disease monitoring with the execution of a function Proc( ). The function Proc( ) also determines whether there remain data to be processed. If this is the case, then the index i is incremented in an operation 385, and the second loop resumes with the operation 350. Otherwise, the function Calc( ) ends in an operation 390.

Based on the computations of the function Calc( ), a set of functionalities may be used, comprising the sending of a warning signal, the display of the computed vectors xc and T, computing of cardiac indicators CI from the vectors xc and T, etc.

Furthermore, the model described above may be supplemented in order to incorporate the introduction of pharmacological elements into the venous system. The effects of these elements may also be taken into account, so as to enable a physician to predict the progression of the patient undergoing the monitoring according to the pharmacological element introduced and the quantity thereof.

In the example described herein, the Applicant shows the example of three elements:
propofol, having an anaesthetic effect,
norepinephrine, having a vasopressor effect, and
infusion of fluids, which is added directly to the liquid volume in the circulation.

In the third case, the effect may be determined directly in that which has been described above. Indeed, adding liquid volume to the circulation modifies the value Veff, and therefore the discretisation of equations (90) and (100).

In the first and the second case, the effect of the pharmacological element on a parameter K in question is modelled according to equation (500), where $\alpha(t)$ is a law of progression of the element according to equation (510) of Appendix A, and K0 a base value of the parameter K in question. The law $\alpha(t)$ may vary as a function of the value of K0, in order to account for a saturation effect.

In equation (510), X represents the concentration of the pharmacological element introduced, $\alpha_\infty(X)$ the increase in K in relative values obtained by a sustained infusion of the pharmacological element at concentration X, and Tx is a time constant which defines the effect rate of the pharmacological element at concentration X.

In the case of propofol (respectively norepinephrine), the cardiac parameters that will be influenced according to equations (500) and (510) will be the cardiac contractility s0, the distal resistance Rd and the distal capacity Cd. Propofol (respectively norepinephrine) has the effect of lowering (respectively increasing) the distal resistance Rd, and of increasing (respectively lowering) the distal capacity Cd. Furthermore, norepinephrine has the effect of increasing cardiac contractility s0. There will therefore be a set of equations per parameter influenced.

Here again, these equations will modify the discretisation of equations (90) and (100), as well as that of equations (30) to (70), and equation (510) will be discretised according to equation (520) of Appendix A.

The laws $\alpha(t)$, $\alpha_\infty(X)$ and the constants Tx may be determined beforehand, by mean on a group of subjects, and optionally undergo an adaptation per subject if applicable.

The computing function may use other cardiovascular models than that given herein by way of example, and receive and pre-process signals measured by other sensors, and particularly those for measuring the indicators providing data on the alignment between the oxygen consumption and supplies in organs such as the brain, heart, kidney and musculocutaneous tissues.

Figure 4:
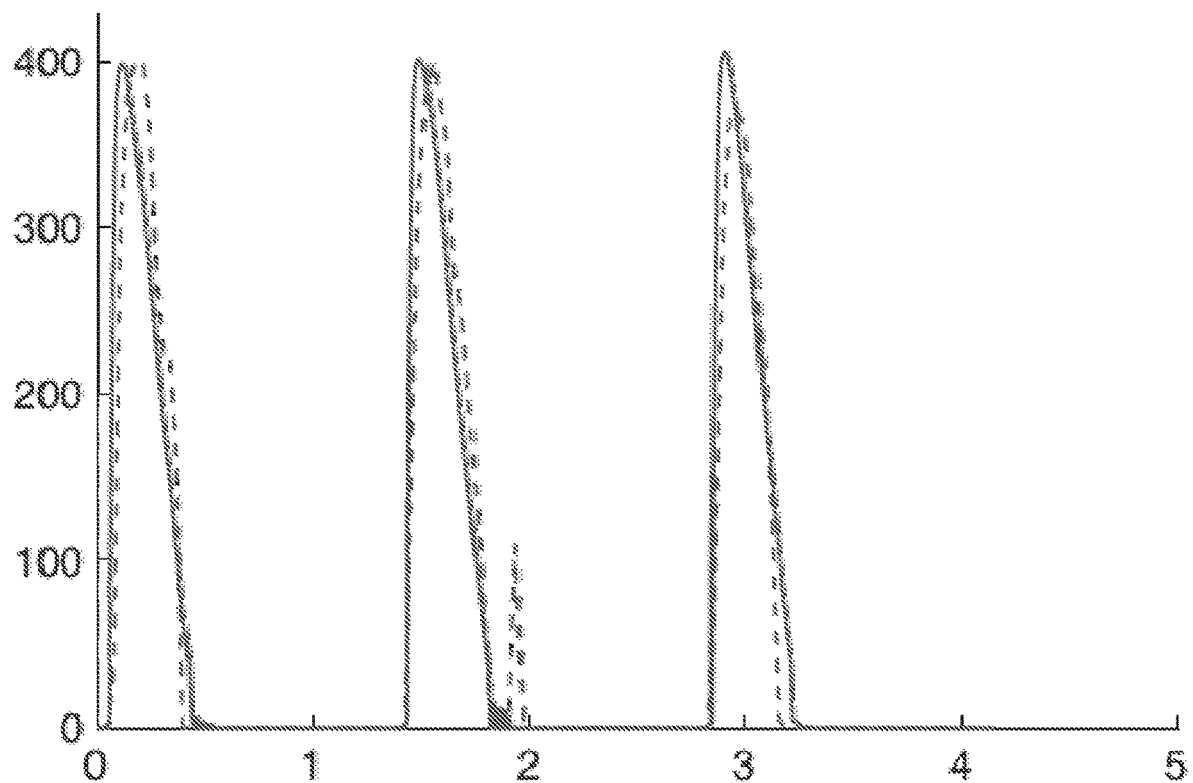
Figure 5:
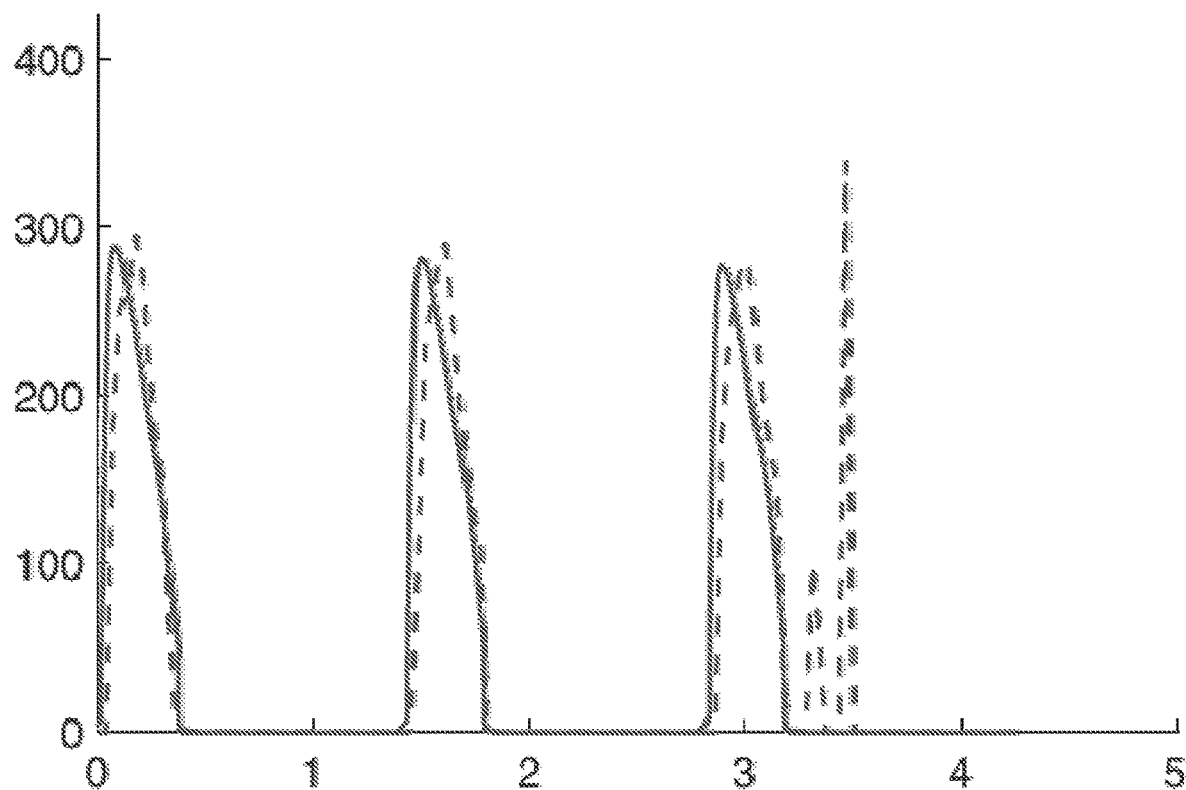

FIGS. 4 and 5 represent on the x-axis the time in s, and on the y-axis the aortic flow in ml/s. In these two figures, the dotted line represents the values measured, and the solid line represents the values simulated by the device in FIG. 1. FIG. 4 represents a scenario without norepinephrine infusion, whereas FIG. 5 represents a scenario with norepinephrine infusion.

Figure 6:
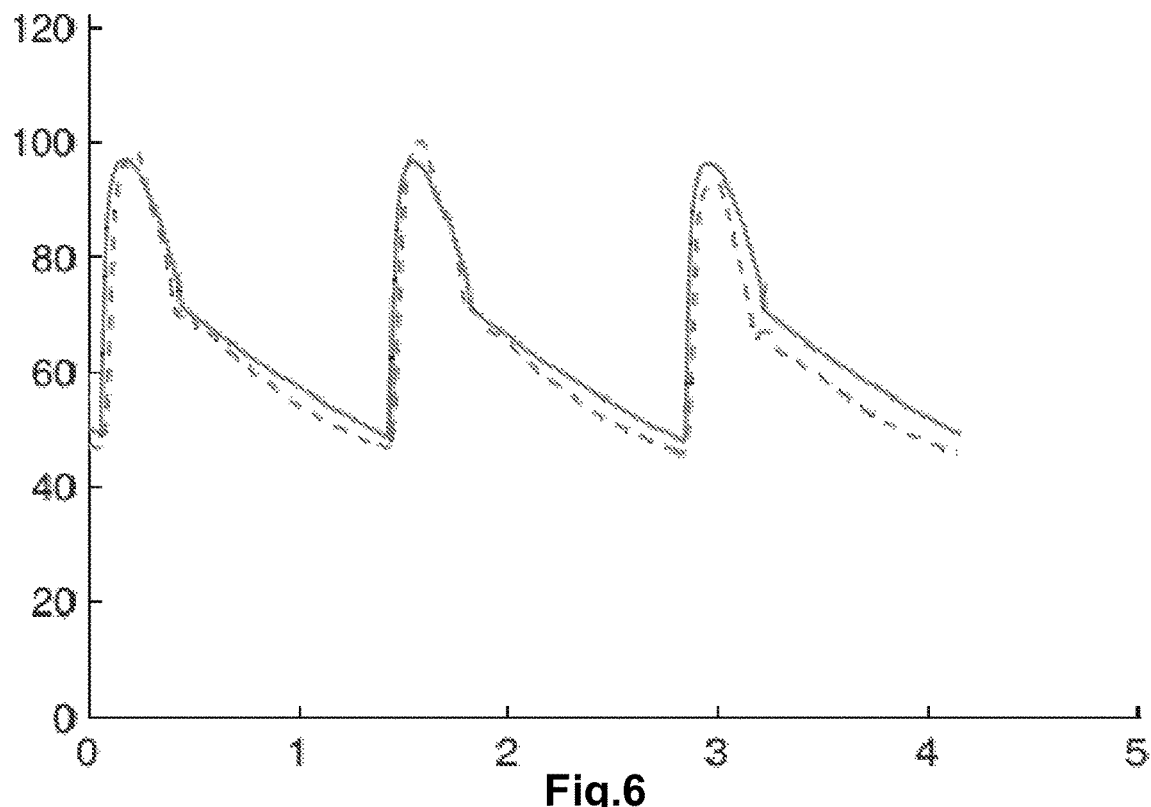
Figure 7:
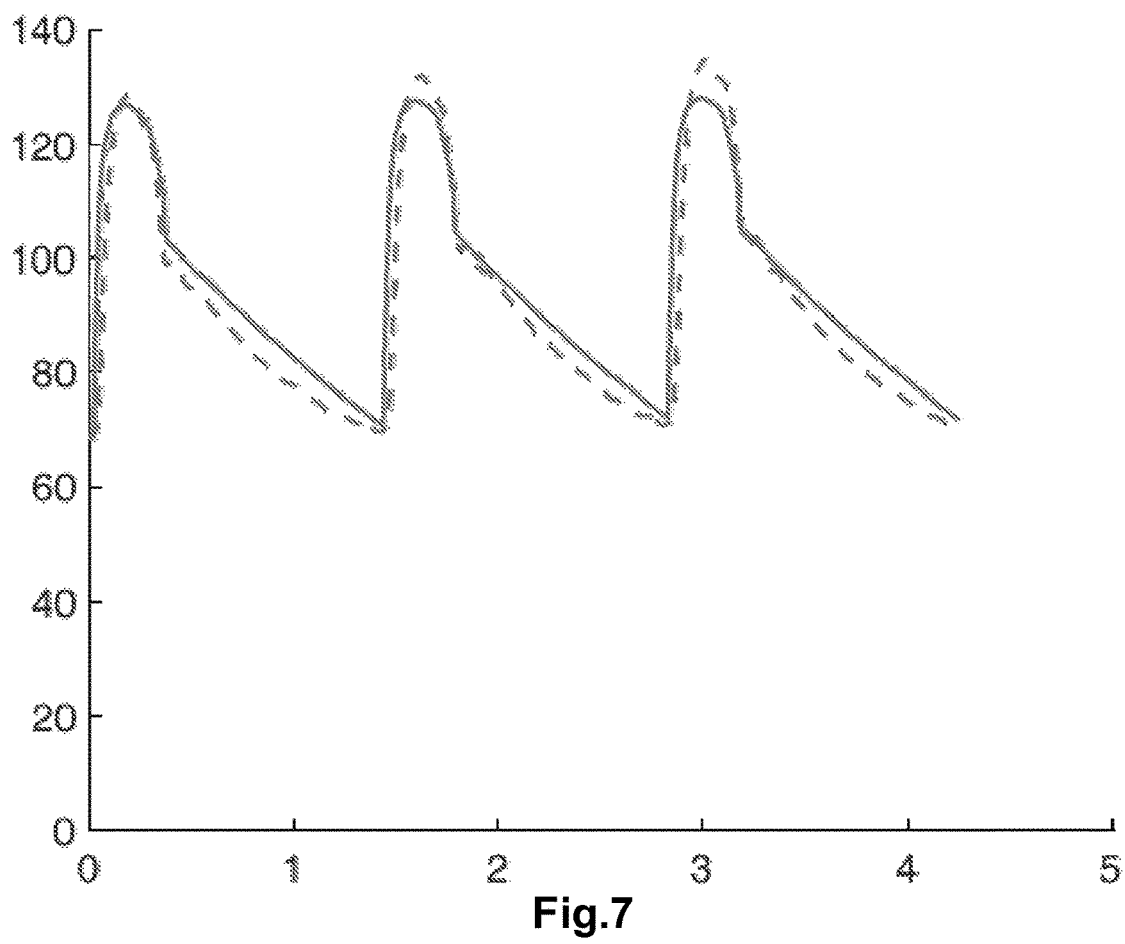

FIGS. 6 and 7 represent on the x-axis the time in s, and on the y-axis the aortic pressure in mmHg. In these two figures, the dotted line represents the values measured, and the solid line represents the values simulated by the device in FIG. 1. FIG. 6 represents a scenario without norepinephrine infusion, whereas FIG. 7 represents a scenario with norepinephrine infusion.

Figure 8:
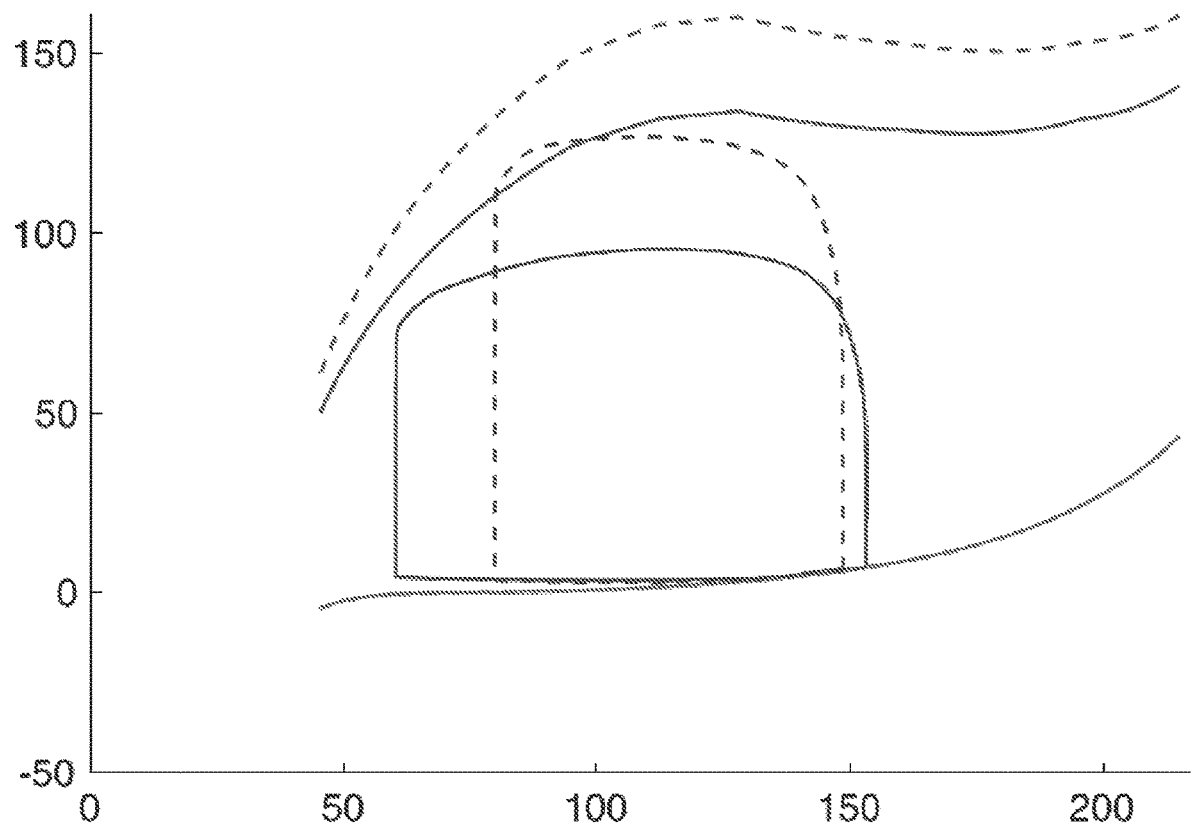

Finally, FIG. 8 represents ventricular pressure (on y-axis, in mmHg)-ventricular volume (on x-axis, in ml) computed by the model calibrated based on the measurements and diastolic/systolic pressure-volume relations. In this figure, the solid lines represent the loops during an idle state, and the dotted lines represent the loops during an administration of norepinephrine.

The closed lines represent the pressure-volume loop, the lines in the upper section represent the telesystolic pressure-volume relation, and the lines in the lower section represent the telediastolic pressure-volume relation.

$$\rho d_0 \ddot{y} + \frac{d_0}{R_0}\left(1 + \frac{y}{R_0}\right)\Sigma_{sph} = P_v\left(1 + \frac{y}{R_0}\right)^2 \tag{10}$$

$$\Sigma_{sph} = \sigma_{1D} + 4(1 - C^{-3})\left(\frac{\partial W_e}{\partial J_2} + C\frac{\partial W_e}{\partial J_2}\right) + 2\frac{\partial W_e}{\partial J_4} + 2\eta \dot{C}(1 - 2C^{-6}) \tag{11}$$

$$\sigma_{1D} = E_s \frac{e_{1D} - e_C}{(1 + 2e_C)^2} \tag{12}$$

$$C = \left(1 + \frac{y}{R_0}\right)^2 \tag{13}$$

$$e_{1D} = \frac{c - 1}{2} \tag{14}$$

$$f_{va}(P_v, P_{ar}, P_{at}) = -4\pi R_0^2 \left(1 + \frac{y}{R_0}\right)^2 \dot{y} \tag{15}$$

$$J_1 = 2C + C^{-2} \tag{16}$$

$$J_4 = C \tag{17}$$

$$W_e(J_1, J_4) = k_1 e^{k_2(J_1 - 3)^2} + k_3 e^{k_4(J_4 - 1)^2} \tag{18}$$

$$(t_C + \mu \dot{e}_c) = E_S \frac{(e_{1D} - e_c)(1 + 2e_{1D})}{(1 + 2e_c)^3} \tag{20}$$

$$\dot{k}_c = -(|\bar{u}| + \alpha|\dot{e}_c|)k_c + n_0 k_0 |\bar{u}|_+ \tag{30}$$

$$\dot{t}_C = -(|\bar{u}| + \alpha|\dot{e}_c|)t_c + n_0 s_0 |\bar{u}|_+ + k_c \dot{e}_c \tag{40}$$

-continued $$C_\mu P_{ar} + \frac{(P_{ar} - P_d)}{R_p} = Q_c \tag{50}$$

$$Q_c = \begin{cases} f_{va}(P_v, P_{ar}, P_{ac}) & \text{si } f_{va}(P_v, P_{ar}, P_{at}) > 0 \\ 0 & \text{si non} \end{cases} \tag{60}$$

$$C_d \dot{P}_d + \frac{(P_d - P_{ar})}{R_p} = \frac{(P_{sv} - P_d)}{R_d} \tag{70}$$

$$\dot{x}_c = A_c(x_c, T, t) \tag{80}$$

$$\frac{V_{eff}}{R_d C_d} - \left(1 + \frac{C_{sv}}{R_d}\right)\frac{P_{sc}(t)}{R_d} = \frac{\int_{t-ST}^{t} e^{-\frac{t-s}{T0}} Q_c(s) ds}{\int_{t-ar}^{t} e^{-\frac{t-s}{T0}} ds} \tag{90}$$

$$P_{at}(t) = P_{sv}(t) + \Delta P_{at}(t) \tag{100}$$

$$z(t) = \begin{bmatrix} P_{ar} \\ Q_c \end{bmatrix} \tag{110}$$

$$I(t) = Z(t) - z(t) \tag{120}$$

$$\dot{x}_c = A_c(x_c, T, t) + K_t(I(t), t) \tag{180}$$

$$\dot{T} = K_T(I(t), t) \tag{185}$$

$$x_c(t_{i+1}) = A_c(x_c(t_i), T(t_i), t_i)(t_{i+1} - t_i) + x_c(t_i) \tag{280}$$

$$z(t_{i+1}) = \begin{bmatrix} \frac{P_{ar}(t_{i+1}) - P_{ar}(t_i)}{(t_{i+1} - t_i)} \\ \frac{Q_c(t_{i+1}) + Q_c(t_i)}{2} \end{bmatrix} \tag{310}$$

$$x_c(t_{i+1}) = (A_c(x_c(t_i), T(t_i), t_i) + K_c(I(t_{i+1}), t_{i+1}))(t_{i+1} - t_i) + x_c(t_i) \tag{380}$$

$$T(t_{i+1}) = K_T(I(t_{i+1}), t_{i+1})(t_{i+1} - t_i) + T(t_i) \tag{395}$$

$$z(t_{i+1}) = \begin{bmatrix} \frac{P_{ar}(t_{i+1}) - P_{ar}(t_i)}{(t_{i+1} - t_i)} \\ \frac{Q_c(t_{i+1}) + Q_c(t_i)}{2} \end{bmatrix} \tag{410}$$

$$K(t) = (1 + \alpha(t))K_0 \tag{500}$$

$$\dot{\alpha}(t) + \frac{\alpha(t)}{T_X} = \frac{\alpha_\infty(X)}{T_X} \tag{510}$$

$$\frac{\alpha(t_{i+1}) - \alpha(t_i)}{(t_{i+1} - t_i)} + \frac{\alpha(t_{i+1}) + \alpha(t_i)}{2T_X} = \frac{\alpha_\infty\left(K\left(\frac{t_{i+1} + t_i}{2}\right)\right)}{T_X} \tag{520}$$

The invention claimed is:

1. Cardiac device for real-time cardiovascular monitoring carried out in anaesthesia and intensive care characterised in that the device comprises a memory arranged for receiving haemodynamic data, and a computer arranged for applying a cardiovascular model comprising a cardiac model and an arterial and venous blood circulation model based on the haemodynamic data received in the memory, and for deriving therefrom at least one cardiac activity indicator (CI), wherein the computer is arranged for computing a cardiac activity indicator (CI), by applying a cardiovascular model to compute an arterial pressure value and a cardiac output value that are theoretical, and by applying at least one correction function based on a difference between the arterial pressure value and the cardiac output value that are theoretical and the haemodynamic data received in the memory.

2. Device according to claim 1, wherein the computer is arranged for applying at least one Kalman filter or a combination of a Kalman filter with a Luenberger observer in said at least one correction function.

3. Device according to claim 1, wherein the computer is further arranged for applying the arterial and venous blood circulation model with a pharmacological model.

4. Cardiac monitoring method for real-time cardiovascular monitoring carried out in anaesthesia and intensive care comprising:
  receiving haemodynamic data,
  applying, with a computer, a cardiovascular model comprising a cardiac model and an arterial and venous blood circulation model to the haemodynamic data, and deriving therefrom at least one cardiac activity indicator (CI), and
  computing, with the computer, a cardiac activity indicator (CI), by applying a cardiovascular model to compute an arterial pressure value and a cardiac output value that are theoretical, and by applying at least one correction function based on a difference between the arterial pressure value and the cardiac output value that are theoretical and haemodynamic data, wherein the at least one correction function is arranged to adjust the cardiovascular model to a patient.

\* \* \* \* \*